(12) United States Patent
Schwartz

(10) Patent No.: US 9,101,333 B2
(45) Date of Patent: Aug. 11, 2015

(54) INTEGRATIVE ATRIAL FIBRILLATION ABLATION

(75) Inventor: Yitzhack Schwartz, Haifa (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 931 days.

(21) Appl. No.: 13/295,594

(22) Filed: Nov. 14, 2011

(65) Prior Publication Data

US 2013/0123773 A1 May 16, 2013

(51) Int. Cl.
*A61B 18/00* (2006.01)
*A61B 5/00* (2006.01)
*A61N 7/02* (2006.01)
*A61B 18/14* (2006.01)
*A61B 18/24* (2006.01)
*A61B 19/00* (2006.01)
*A61B 5/0452* (2006.01)

(52) U.S. Cl.
CPC ............ *A61B 5/7285* (2013.01); *A61B 5/0452* (2013.01); *A61B 18/1492* (2013.01); *A61B 18/24* (2013.01); *A61B 19/5244* (2013.01); *A61B 19/56* (2013.01); *A61B 2018/00357* (2013.01); *A61B 2018/00577* (2013.01); *A61B 2019/465* (2013.01); *A61B 2019/5289* (2013.01); *A61B 2019/562* (2013.01); *A61N 7/022* (2013.01)

(58) Field of Classification Search
CPC .. A61B 5/7285; A61B 18/1792; A61B 18/24; A61N 7/022
USPC ............ 606/41; 600/509, 510, 512, 518, 523
See application file for complete search history.

(56) References Cited

U.S. PATENT DOCUMENTS

| 6,226,542 B1 | 5/2001 | Reisfeld |
| 6,236,883 B1 | 5/2001 | Ciaccio |
| 6,292,695 B1 | 9/2001 | Webster, Jr. et al. |
| 6,301,496 B1 | 10/2001 | Reisfeld |

(Continued)

FOREIGN PATENT DOCUMENTS

| EP | 2 462 867 A1 | 6/2012 |
| WO | WO 2012/151301 A1 | 11/2012 |

OTHER PUBLICATIONS

Lemery R. et al., "Feasability study of endocardial mapping of ganglionated plexuses during catheter ablation of atrial fibrillation", Heart Rhythm (Apr. 1, 2006), vol. 3, No. 4, pp. 387-396.

(Continued)

*Primary Examiner* — Christopher D Koharski
*Assistant Examiner* — Michael Carey
(74) *Attorney, Agent, or Firm* — Louis J. Capezzuto

(57) ABSTRACT

Cardiac tissue ablation is carried out by defining first regions containing first locations including ganglionated plexi in a heart of a living subject, and inserting a probe into the heart. The method is further carried out by detecting electrical activity in the heart via electrodes on the distal portion of the probe, defining second regions having second locations, wherein the electrical activity exhibits a dominant frequency that is higher than a predefined threshold, defining third regions having third locations, wherein the electrical activity exhibits complex fractionated atrial electrograms, constructing an electroanatomical map of the heart that defines intersections of the first regions and at least one of the second regions and the third regions, selecting ablation sites within the intersections, and ablating cardiac tissue at the ablation sites.

19 Claims, 5 Drawing Sheets

(56) References Cited

U.S. PATENT DOCUMENTS

| | | | |
|---|---|---|---|
| 6,716,166 | B2 | 4/2004 | Govari |
| 6,773,402 | B2 | 8/2004 | Govari et al. |
| 6,814,733 | B2 | 11/2004 | Schwartz et al. |
| 6,892,091 | B1 | 5/2005 | Ben-Haim et al. |
| 6,997,924 | B2 | 2/2006 | Schwartz et al. |
| 7,156,816 | B2 | 1/2007 | Schwartz et al. |
| 7,229,415 | B2 | 6/2007 | Schwartz |
| 7,536,218 | B2 | 5/2009 | Govari et al. |
| 7,907,994 | B2 | 3/2011 | Stolarski et al. |
| 2004/0015070 | A1 | 1/2004 | Liang |
| 2004/0162507 | A1 | 8/2004 | Govari |
| 2004/0162550 | A1 | 8/2004 | Govari et al. |
| 2004/0225331 | A1 | 11/2004 | Okerlund |
| 2005/0101946 | A1 | 5/2005 | Govari et al. |
| 2006/0287648 | A1 | 12/2006 | Schwartz |
| 2007/0060832 | A1 | 3/2007 | Levin |
| 2007/0197929 | A1 | 8/2007 | Porath et al. |
| 2008/0058657 | A1 | 3/2008 | Schwartz et al. |
| 2009/0005845 | A1* | 1/2009 | David et al. .................... 607/122 |
| 2009/0192393 | A1 | 7/2009 | Hayam et al. |
| 2011/0152856 | A1 | 6/2011 | Govari et al. |
| 2011/0230775 | A1* | 9/2011 | Barley et al. ................... 600/508 |
| 2011/0251505 | A1* | 10/2011 | Narayan et al. ................ 600/515 |

OTHER PUBLICATIONS

Extended European Search Report dated Feb. 28, 2013 from related European Application No. 12192456.7.

Kumagai, K., et al. "Combined Dominant Frequency and Complex Fractionated Atrial Electrogram Ablation After Circumferential Pulmonary Vein Isolation of Atrial Fibrillation" Journal of Cardiovascular Electrophysiology (2013), pp. 1-28. doi: 10.1111/jce.12166.

Abbara, S. et al. Mapping Epicardial Fat With Multi-Detector Computed Tomography to Facilitate Percutaneous Transepicardial Arrhythmia Ablation. European Journal of Radiology;57, 2006; pp. 417-422.

Chiou, C.W. et al. Selective Vagal Denervation of the Atria Eliminates Heart Rate Variability and Baroreflex Sensitivity While Preserving Ventricular Innervation, Circulation, 1998;98:36-368.

Dewire, J. et al. Current Anatomical/Arrhythmic Mechanisms of AF. Nat. Rev. Cardiol. Doi:10.1038/nrcardio.2009.232.

Dewire, J. et al. State-of-the-Art and Emerging Technologies for Atrial Fibrillation Ablation. Nature Reviews/Cardiology; vol. 7, Mar. 2010, pp. 129-138.

Dorostkar P. C. et al. Electronatomical Mapping and Ablation of the Substrate Supporting Intraatrial Reentrant Tachycardia After Palliation for Complex Congenital Heart Disease, Pacing and clinical Electrophysiology; Sep. 1, 1998; pp. 1810-1819; vol. 21, No. 9, Blacwell Futura Publishing, Malden, MA USA.

Flotats, A. et al. Proposal for Standardization of 123 I-Metaiodobenzylguanidine (MIBG) cardiac sympathetic imaging by the EANM Cardiology. Eur J Nucl Med Mol Imaging (2010) 37:1802-1812.

Hasteneufel M. et al, A Novel Method for Planning and Visualization of Ablation Lines for Atrial Fibrillation Treatment, Computers in Cardiology, Sep. 1, 2004, pp. 13-16; IEEE, Piscataway, NJ USA.

Hou, Y. et al. Ganglionated Plexi Modulate Extrinsic Cardiac Autonomic Nerve Input, Journal of the American College of Cardiology, vol. 50, No. 1, 2007.

Hou, Y. et al. Ganglionated Plexi Modulate Extrinsic Cardiac Autonomic Nerve Input, Journal of the American College of Cardiology, vol. 50, No. 2, 2007, pp. 61-68.

Jackman et al. Catheter Ablation of Cardiac Autonomic Nerves for Prevention of Vagal Atrial Fibrillation, Circulation, 2000;102:2774-2780.

Kriegshauser, J.S. et al. MR Imaging of Fat in and Around the Heart. AJR 155:271-274, Aug. 1990.

Kuck, K.H. et al. A Novel Radiofrequency Ablation Catheter Using Contact Force Sensing: Toccata Study. Heath Rhythm, Manuscript, Doi:10.1016/hrthm.2011.08.021.

Lazar, S. et al. Presence of Left-to-Right Atrial Frequency Gradient in Paroxysmal But Not Persistent Atrial Fibrillation in Humans, Circulation, 2004;110:3181-3186.

Lu, Z. et al. Functional Properties of the Superior Vena Cava (SVC)—Aorta Ganglionated Plexus, J Cardiovasc Electrophysiol. vol. pp. 1-8, 2010.

Nadamanee et al., A New Approach for Catheter Ablation of Atrial Fibrillation: Mapping of the Electrophysiologic Substrate, J. Am Coll. Cardiol., 2004;43(11):2044-2053.

Nakagawa, H., M.D. PhD. et al. Localization of Left Atrial Autonomic Ganglinated Plexuses Using Endocardial and Epicardial High Frequency Stimulation in Patients With Atrial Fibrillation, Heart Rhythm, vol. 2, No. 5, AB6-1 May Supplement 2005.

Ng, J. Technical Considerations for Dominant Frequency Analysis, J Cardiovasc Electrophysiol, vol. 18, pp. 1-8, Jun. 2007.

Perna, F. et al. Assessment of Catheter Tip Contact Force Resulting in Cardiac Perforation in Swine Atria Using Force Sensing Technology, Circ Arrhythm Electrophysiol, 2011;4:218-224.

Rozovsky, K. et al. Added Value of SPECT/CT for Correlation of MIBG Scintigraphy and Diagnostic CT in Neuroblastoma and Pheochromocytoma. AJR, 2008;190:1085-1090.

Sanders, P, et al. Spectral Analysis Identified Sites of High-Frequency Activity Maintaining Atrial Fibrillation in Humans, Circulation, 2005;112:789-797.

Schauerte, P. et al. Catheter Ablation of Cardiac Autonomic Nerves for Prevention of Vagal Atrial Fibrillation, Circulation, 2000;102:2774-2780.

Schwartzman D. et al. Anatomy-Guided Linear Atrial Lesions for Radiofrequency Catheter Ablation of Atrial Fibrillation, Pace—Pacing and Clinical Electrophysiology, Oct. 1, 1998; pp. 1959-1978; vol. 21, No. 10; Blacwell Futura Publishing, Malden, MA USA.

Shah, D. et al. Catheter Tip Force Required for Mechanical Performation of Porcine Cardiac Chambers. Europace, doi:10.1093/Europace/euq403, 2010.

Soejima, K. et al. Subxiphoid Surgical Approach for Epicardial Catheter-Based Mapping and Ablation in Patients With Prior Cardiac Surgery or Difficult Pericardial Access, Circulation, 2004;110:1197-1201.

Verma, A. et al. Relationship Between Complex Fractionated Electrograms (CFE) and Dominant Frequency (DF) Sites and Prospective Assessment of Adding DF-Guided Ablation to Pulmonary Vein Isolation in Persistent Atrial Fibrillation (AF), J Cardiovasc Electrophysiol, vol. pp. 1-8, 2011.

* cited by examiner

INTEGRATIVE ATRIAL FIBRILLATION ABLATION

BACKGROUND OF THE INVENTION

1. Field of the Invention

This invention relates to relates generally to minimally invasive treatment of organs inside the body. More particularly, this invention relates to determination of ablation sites for ablation treatments applied to cardiac tissue.

2. Description of the Related Art

The meanings of certain acronyms and abbreviations used herein are given in Table 1.

TABLE 1

Acronyms and Abbreviations

| | |
|---|---|
| AF | Atrial Fibrillation |
| CFAE | Complex Fractionated Atrial Electrogram |
| DF | Dominant Frequency |
| GP | Ganglionated Plexi |
| LA | Left Atrium |
| MIBG | $^{123}$I-metaiodobenzylguanidine |
| MRI | Magnetic Resonance Imaging |
| SPECT | Single Photon Emission Computed Tomography |

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Successful catheter-based ablation for atrial fibrillation (AF) often entails accurate execution of a relatively complex therapeutic plan comprising many ablation points. The procedure is challenging and time consuming. For example, in the document *A New Approach for Catheter Ablation of Atrial Fibrillation: Mapping of the Electrophysiologic Substrate*, Nademanee et al., J. Am. Coll. Cardiol., 2004; 43(11): 2044-2053, it was proposed that atrial fibrillation may be treated by ablating sites exhibiting a complex fractionated atrial electrogram (CFAE). The authors identified areas of CFAE during atrial fibrillation, and then applied radiofrequency ablation to these areas. As a result of the ablation, the atrial fibrillation was resolved in the large majority of the cases.

Nademanee's method requires a human operator to read electrograms to identify sites of CFAE. Commonly assigned U.S. Patent Application Publication No. 2007/0197929, which is herein incorporated by reference, facilitates the procedure by disclosing automated detection and mapping of areas of complex fractionated electrograms within cardiac chambers. Commonly assigned U.S. Patent Application Publication No. 20090192393, which is herein incorporated by reference, discloses automatic detection and mapping of ganglionated plexi that are found within areas of complex fractionated electrograms in cardiac chambers. Functional maps indicating a spatial distribution of the ganglionated plexi and the relative numbers of complex fractionated electrograms are produced for display.

More recently, SPECT and planar cardiac sympathetic imaging using $^{123}$I-metaiodobenzylguanidine (MIBG) has become sufficiently well known to indicate standardization, as described by Albert Flotats et al., *Proposal for standardization of $^{123}$I-metaiodobenzylguanidine (MIBG) cardiac sympathetic imaging by the EANM Cardiovascular Committee and the European Council of Nuclear Cardiology*, Eur J Nucl Med Mol Imaging (2010) 37:1802-1812. Techniques disclosed in Rozovsky et al., *Added Value of SPECT/CT for Correlation of MIBG Scintigraphy and Diagnostic CT in Neuroblastoma and Pheochromocytoma*, AJR 2008; 190: 1085-1090 may be adapted for imaging ganglionated plexi in the heart.

Evaluation of epicardial fat may also be useful in identifying ablation points. For example, commonly assigned U.S. Patent Application Publication No. 2008/0058657, which is herein incorporated by reference, describes obtaining an endocardial map by constructing a matrix relationship between a small number of endocardial points and a large number of external receiving points using a multi-electrode chest panel. Magnetic resonance imaging (MRI) and computed tomography have also been applied to the evaluation of epicardial fat, as described for example in Abbara et al., *Mapping Epicardial Fat With Multi-Detector Computed Tomography To Facilitate Percutaneous Transepicardial Arrhythmia Ablation*, European Journal of Radiology 57 (2006) 417-422, and in Kriegshauser et al., *MR Imaging of Fat in and Around the Heart*, AJR 155:271-274, August 1990.

It has been noted in Dewire, J. & Calkins, State-of-the-art and Emerging Technologies for Atrial Fibrillation Ablation, H. Nat. Rev. Cardiol. 7, 129-138 (2010) that there is an interest in the development of new tools and strategies that will improve the safety and efficacy of AF ablation, shorten procedure time, and allow ablation to be performed by operators with little prior experience of the technique.

SUMMARY OF THE INVENTION

There is provided according to embodiments of the invention a method of ablation, which is carried out by defining first regions containing first locations including ganglionated plexi in a heart of a living subject, and inserting a probe into the heart, the probe having electrodes on a distal portion thereof. The method is further carried out by detecting electrical activity in the heart via the electrodes, defining second regions having second locations, wherein the electrical activity exhibits a dominant frequency that is higher than a predefined threshold, defining third regions having third locations, wherein the electrical activity exhibits complex fractionated atrial electrograms, constructing an electroanatomical map of the heart that defines intersections of the first regions and at least one of the second regions and the third regions, selecting ablation sites within the intersections, and ablating cardiac tissue at the ablation sites.

An aspect of the method includes defining fourth regions, wherein a contact pressure between the probe and a wall of the heart exceeds a predefined pressure threshold, and wherein the intersections defined in the electroanatomical map comprise intersections of the first regions, the second regions, the third regions and the fourth regions.

According to another aspect of the method, defining first regions includes electrically stimulating the heart at a stimulation frequency that exceeds a stimulation threshold.

According to one aspect of the method, defining first regions comprises evaluating epicardial fat pads of the heart.

According to a further aspect of the method, defining first regions is performed by at least one of sympathetic cardiac imaging, magnetic resonance imaging, computed tomographic imaging and multi-detector computed tomography.

According to another aspect of the method, the first regions, the second regions and the third regions are 3-dimensional, and wherein constructing an electroanatomical map includes displaying the electroanatomical map as at least one 2-dimensional projection.

According to yet another aspect of the method, constructing an electroanatomical map includes defining intersections of the first regions, the second regions and the third regions.

Still another aspect of the method includes defining segments of the heart, wherein defining first regions, defining second regions, defining third regions, and selecting ablation sites are performed separately for each of the segments.

According to an additional aspect of the method, selecting ablation sites is performed by random selection within the intersections.

According to one aspect of the method, selecting ablation sites is performed by choosing ones of the second locations and the third locations within the intersections.

Other embodiments of the invention provide apparatus for carrying out the above-described method.

BRIEF DESCRIPTION OF THE SEVERAL
VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Figure 1:
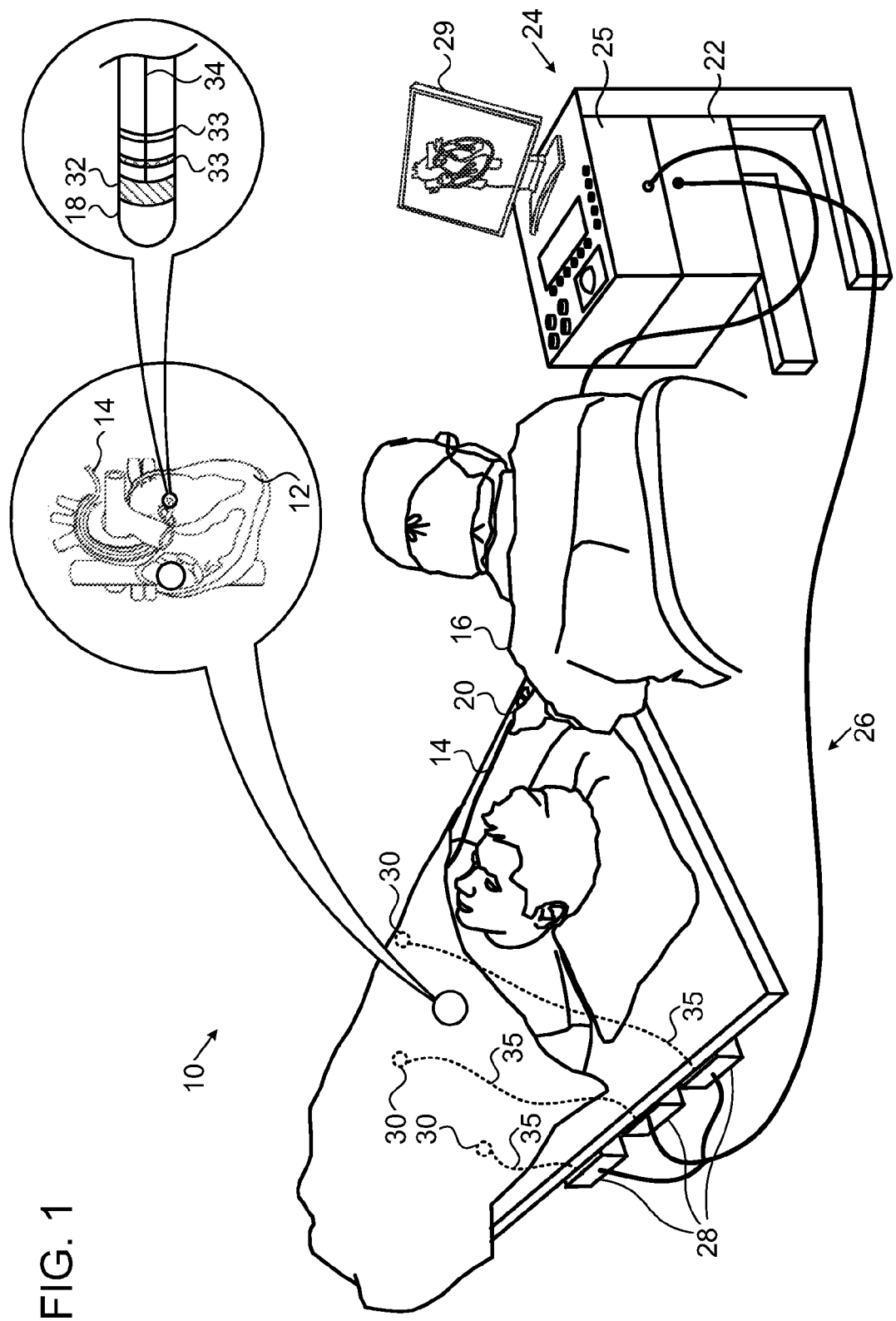
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. An operator 16, who is typically a physician, brings the catheter's distal tip 18 into contact with the heart wall. Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Sensing electrodes 33, also connected to the console 24 are disposed generally in the distal portion of the catheter 14, and have connections to the cable 34. Pacing signals and various other signals may be conveyed from the console 24 through the cable 34 and the electrodes 32, 33 to and from the heart 12. Many configurations of the electrodes 32, 33 are possible. For example the ablation electrode 32 may be disposed at the distal tip 18.

Wire connections 35 link the console 24 with body surface electrodes 30 and other components of a positioning subsystem. The ablation electrode 32, the sensing electrodes 33 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near the ablation electrode 32. While shown as a ring electrode in FIG. 1, the ablation electrode 32 may be a tip electrode. Optionally, more than one instance of the ablation electrode 32 may be mounted on the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning system 26 of the system 10 that measures location and orientation coordinates of the catheter 14.

In one embodiment, the positioning system 26 comprises a magnetic position tracking arrangement that determines the position and orientation of the catheter 14 by generating magnetic fields in a predefined working volume its vicinity and sensing these fields at the catheter using field generating coils 28 and may include impedance measurement, as taught, for example in U.S. Patent Application Publication No. 2007/0060832, which is herein incorporated by reference. The positioning system 26 may be enhanced by position measurements using the impedance measurements described in the above-noted U.S. Pat. No. 7,536,218.

As noted above, the catheter 14 is coupled to the console 24, which enables the operator 16 to observe and regulate the functions of the catheter 14. Console 24 includes a processor, which can be a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system 26 to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Moreover, the system 10 has facilities for registering images produced by other modalities, e.g., the CT, MRI, and nuclear images as described above with current and previously generated electro-anatomic maps of the heart 12. The CARTOMERGE™ Image Integration Module, available from Biosense Webster is suitable.

Figure 2:
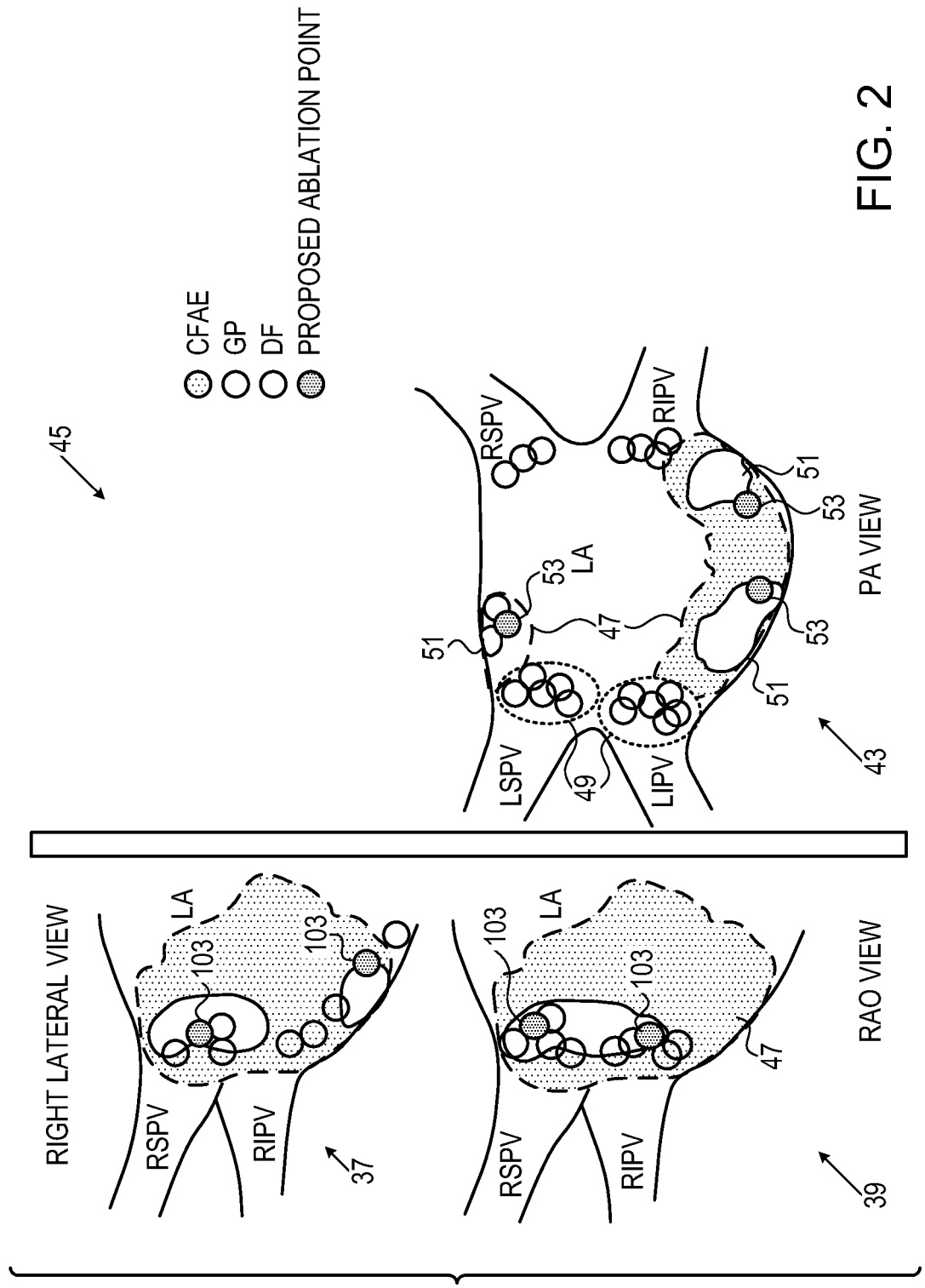
FIG. 2 is a series of diagrams based on data collected from a series of patients who underwent cardiac catheterization that illustrates selection of ablation sites in accordance with an embodiment of the invention.

Reference is now made to FIG. 2, which is a series of diagrams based on data collected from a series of patients who underwent cardiac catheterization that illustrates selection of ablation sites in accordance with an embodiment of the invention. The diagrams represent mappings of a left atrium in a right lateral view 37, right anterior oblique view 39 (RAO) and posterior-anterior view 43. As noted above, arrhythmogenic zones are associated with areas containing ganglionated plexi and with demonstrable complex fractionated atrial electrograms. Moreover, frequency gradients are known to exist in hearts exhibiting atrial fibrillation and can be identified by electroanatomical mapping, for example, using the above-noted CARTO 3 system. Ablation of sites having electrical activity exhibiting high dominant frequencies (DF) that exceed a predefined threshold often results in prolongation of cycle length and termination of the arrhythmia. The threshold criteria applied to power spectra of the electrograms that are described in Sanders et al., *Spectral Analysis Identifies Sites of High-Frequency Activity Maintaining Atrial Fibrillation in Humans, Circulation.* 2005; 112:789-797, herein incorporated by reference, are suitable for defining sites having high DF.

A key 45 at the right of the figure indicates three features of the mappings that are taken into consideration when ablation points are selected: FIG. 2 demonstrates regions 47 containing CFAE, regions 49 containing dominant frequency sites, and regions 51 containing ganglionated plexi. Definition of these regions is described below. Proposed ablation points 53 are shown. The first, second and third regions are actually 3-dimensional, but are shown in 2-dimensional projections in FIG. 2. Sites containing CFAE may be determined using the techniques described in the above-noted U.S. Patent Application Publication No. 20090192393. Sites having a dominant frequency can be determined according to the teachings of commonly assigned U.S. Pat. No. 7,907,994 to Stolarski, et al., which is herein incorporated by reference. Alternatively, the CARTO 3 system may be employed for electroanatomical mapping to identify CFAE and dominant frequency sites, augmented by visualization of ganglionated plexi using cardiac sympathetic imaging with MIBG. The CARTO 3 system enables the MIBG images to be placed in registration with the electroanatomical maps. However, these features may be located by any of the methods described hereinabove and combinations thereof.

Figure 3:
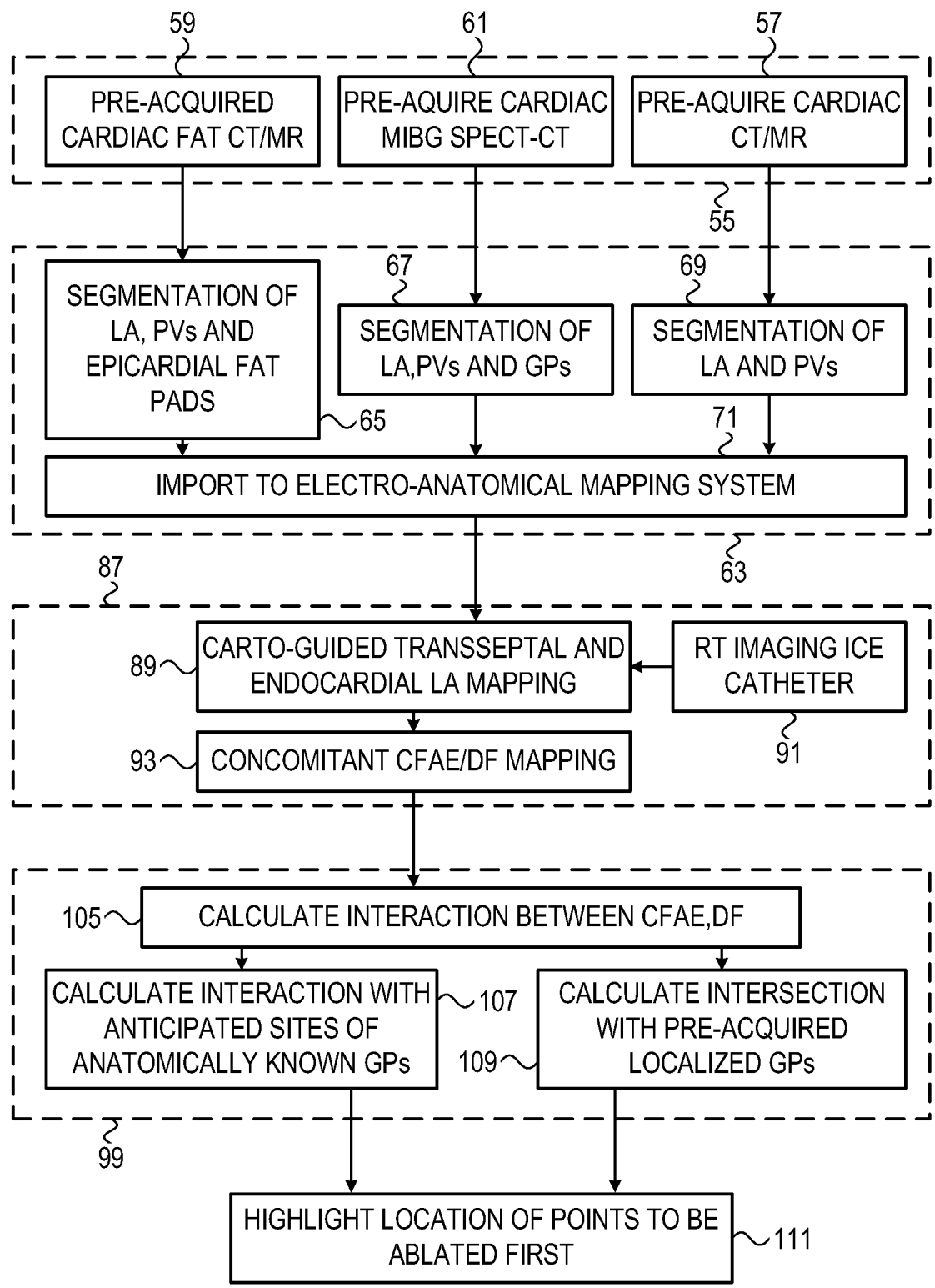
FIG. 3 is a flow chart of a method of integrating data collected using a plurality of methods to select ablation points for treatment of atrial fibrillation and other cardiac arrhythmias in accordance with an embodiment of the invention.

Reference is now made to FIG. 3, which is a flow chart of a method of integrating data collected using a plurality of modalities to optimally select ablation points for treatment of atrial fibrillation and other cardiac arrhythmias in accordance with an embodiment of the invention. The process steps are shown in a particular linear sequence in FIG. 3 for clarity of presentation. However, it will be evident that many of them can be performed in parallel, asynchronously, or in different orders. Moreover, not all illustrated process steps may be required to implement the process.

In a first phase 55 cardiac data is acquired by any combination of several modalities. Typically, but not necessarily, first phase 55 occurs prior to cardiac catheterization. The cardiac anatomy may be imaged by at least one of CT and MRI methods at step 57. Evaluation of cardiac fat to locate ganglionated plexi may be performed using the same or different CT and/or MRI studies at step 59. MIBG imaging using hybrid CT and single photon emission computed tomography (SPECT) may be performed in step 61 in order to more precisely locate the ganglionated plexi.

In a second phase 63 the images acquired in the first phase 55 are segmented, such that only the relevant anatomical structures required for preplanning and execution of an atrial fibrillation ablation are available in 3D and at high resolution. The left atrium, pulmonary veins and epicardial fat pads are defined as appropriate for the particular images obtained in first phase 55. Thus, in step 65, the left atrium, pulmonary veins (PVs) and epicardial fat pads are defined in the images acquired in step 59. In step 67, the left atrium, pulmonary veins and ganglionated plexi are identified in the MIBG images acquired in step 61. When epicardial fat pads are analyzed, the ganglionated plexi locations are inferred. In step 69 The left atrium and pulmonary veins are identified in the images acquired in step 57.

At step 71 the images processed in second phase 63 are imported into an electro-anatomic mapping system, e.g., the CARTO 3 system. Step 71 can be performed using the above-noted CARTOMERGE image integration module.

Figure 4:
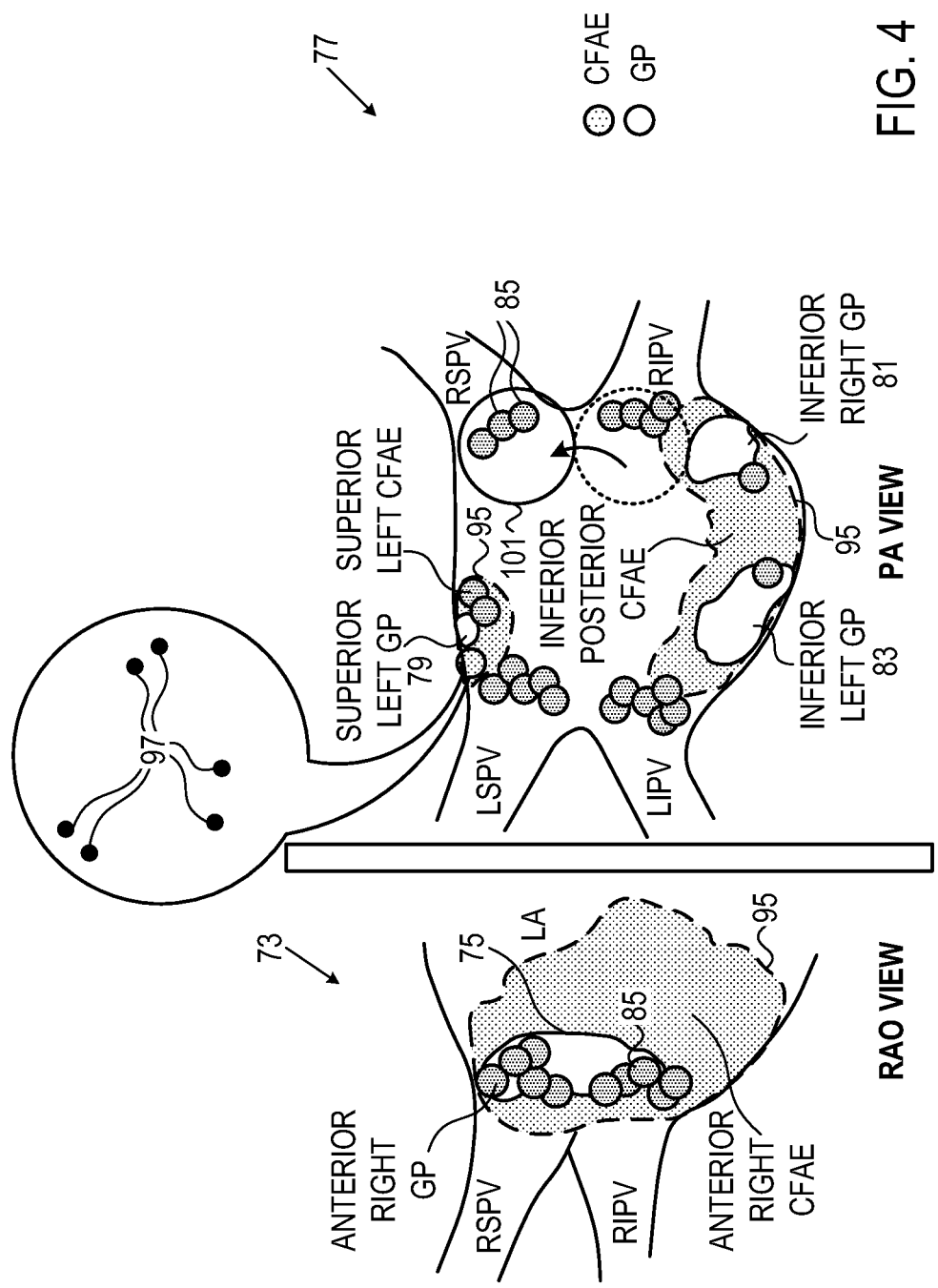
FIG. 4 illustrates importation and registration of pre-acquired images into an electroanatomical map in accordance with an embodiment of the invention.

Reference is now made to FIG. 4, which illustrates the importation and registration of pre-acquired images into an electroanatomical map in accordance with an embodiment of the invention. In a right anterior oblique view 73 (RAO view), the right superior pulmonary vein (RSPV), right inferior pulmonary vein (RIPV) and left atrium (LA) are defined. A region 75 containing the anterior right ganglionated plexus is indicated. In a posterior-anterior (PA) view 77 the RSPV, RIPV, left superior pulmonary vein (LSPV) and left inferior pulmonary vein (LIPV) are shown. The view 77 further indicates the superior left, inferior right and inferior left ganglionated plexi as regions 79, 81, 83, respectively. Circles 85 (FIG. 4) indicate sites having a dominant frequency.

Reverting to FIG. 3, in a third phase 87 cardiac catheterization is performed. Anatomic mapping of the left atrium is performed in step 89. This may be accomplished using the CARTO 3 system by transseptal and endocardial mapping. A technique for transseptal mapping is described, for example, in commonly assigned U.S. Pat. No. 7,229,415 to Schwartz, which is herein incorporated by reference. Optionally, step 89 may be performed concurrently with realtime ultrasound imaging in step 91, for example using an Ultra ICE™ catheter, available from Boston Scientific, One Boston Scientific Place, Natick, Mass. 01760-1537.

In step 93 electroanatomical mapping is performed, typically concomitantly with step 89. Referring again to FIG. 4, second regions containing dominant frequency sites (circles 85) and third regions showing CFAE are mapped in step 93, together with the ganglionated plexi-containing regions 75, 79, 81, 83. CFAE-containing regions 95 are represented as areas on the map. However these areas are defined by a number of discrete sampled points 97 on the endocardium in which CFAE were demonstrated, as described in the above-noted U.S. Patent Application Publication No. 2007/0197929.

In a fourth phase 99 (FIG. 3), the points and regions developed and mapped in the third phase 87 are processed in order to select a set of ablation points. This is done by identifying intersections of areas containing ganglionated plexi, CFAE, and dominant frequency sites. In one method the intersections are identified by moving a circular area 101 of 10 mm diameter about the electroanatomical map in discrete steps. At each position of the circular area 101, points therein belonging to the relevant categories (referred to as "hits") are identified. As noted above, the categories are ganglionated plexi, points showing CFAE, and points of dominant frequency.

As best seen in the right lateral view 37 and right anterior oblique view 39 (FIG. 2), points 103 lying in the "intersection" of regions containing CFAE, dominant frequency and ganglionated plexi (as determined by evaluation of cardiac fat) are identified as candidates for selection as ablation points. The pseudocode of Listing 1 presents one method for making the determination:

Listing 1

For each segment of LA (as defined in second phase 63)
  Position 10 mm circular window on map reconstruction in current segment
  Define first regions containing ganglionated plexi based on expected anatomic locations (regions 51, FIG. 2);
  Do
    Record CFAE "hits" in window in First region Record hits indicating dominant frequency site in window
    Move circular window to new position in segment
  Loop until all first regions in current segment are Evaluated
  Define second regions containing dominant frequency sites (regions 49, FIG. 2);
  Define third regions containing CFAE (regions 47, FIG. 2). Generally the regions are defined such that the acquired points are relatively evenly distributed. This reduces the sample size required to obtain meaningful information. The above-noted CARTO 3 system provides operator-assisted facilities for defining endocardial regions of enterest;
  Identify first intersections of second regions (CFAE) with third regions (DF) (step 105, FIG. 3).
  Identify second intersections of the first intersections and sites of ganglionated plexi by performing at least one of steps 107, 109. (If one of the first regions and second regions does not exist, then treat the other of the first regions and second regions as the first intersection.
  Select at random N points in each of the second intersections for ablation (final step 111). The selected N points should coincide with the points corresponding to the CFAE or DF hits.
  Optionally, rank the areas covered by the moving windows according to the number of hits, and limit the selection of the N points in the preceding step to highly ranked areas, disregarding the lower ranked areas. A cut-off may be set by the operator, or chosen arbitrarily, for example, the areas only in the highest quartile may be subject to selection.
next segment.

In final step 111 ablation points are selected from candidates within the intersections. The selection process may be automatic, for example using the above-noted CARTO 3 system, or operator-assisted. The ablation points may be recommended randomly within the intersections. Alternatively, the ablation points may be selected by the operator from points that were identified during the catheterization as exhibiting both dominant frequency sites and CFAE.

Alternatively, rather than segmenting the left atrium, the hit-containing areas may be evaluated globally within the left atrium. The chosen ablation points may be high-lighted on a display for the operator. Ablation may then proceed at the chosen sites. In general, fewer than all the candidates are selected as ablation points. This reduces operating time and patient morbidity.

Alternate Embodiment 1

With continued reference to FIG. 3, in this variant, the mapping process described in the third phase 87 is augmented by including a map of the contact force between the catheter and the endocardium during the electroanatomic mapping process (step 89). The cardiac catheter incorporates a pressure detector for sensing a mechanical force against the distal tip when engaging an ablation site. A contact for catheter of the sorted described in commonly assigned U.S. Pat. No. 8,926,604, which is herein incorporated by reference, may be used for this purpose. A suitable contact force catheter is available from Biosense-Webster as the THERMOCOOL® SMARTTOUCH™ Contract Force Sensing Catheter. Regions having points in which the contact force exceeds a threshold value are defined (CF regions). In these regions only local effects contribute are perceived in the sensor; far field effects are filtered out. A contact force of at least 7 g is suggested.

Figure 5:
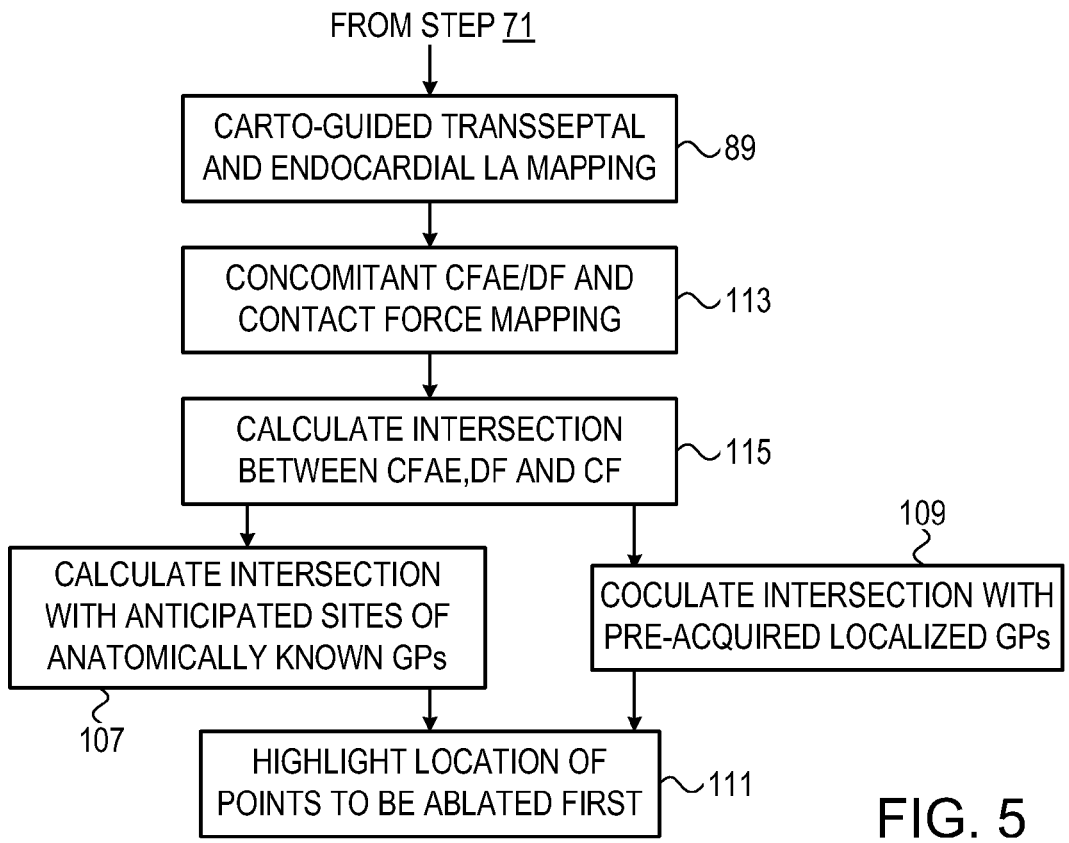
FIG. 5 is a portion of the flow chart shown in FIG. 3, which has been modified in accordance with an alternate embodiment of the invention.

Reference is now made to FIG. 5, which is a portion of the flow chart shown in FIG. 3, and which has been modified in accordance with an alternate embodiment of the invention. After performing step 89 (FIG. 3), in step 113 electroanatomical mapping is performed as in step 93 (FIG. 3), and concomitantly with contact force mapping.

Next, step 115 is similar to step 105 (FIG. 3), except intersections are determined between the second regions (CFAE) with third regions (DF) and the CF regions. The procedure then continues in the same manner as described above with respect to FIG. 3. Limiting the selection of ablation points to areas having sufficiently high contact force prevents far field effects from interfering with the selection of ablation sites.

Alternate Embodiment 2

Figure 6:
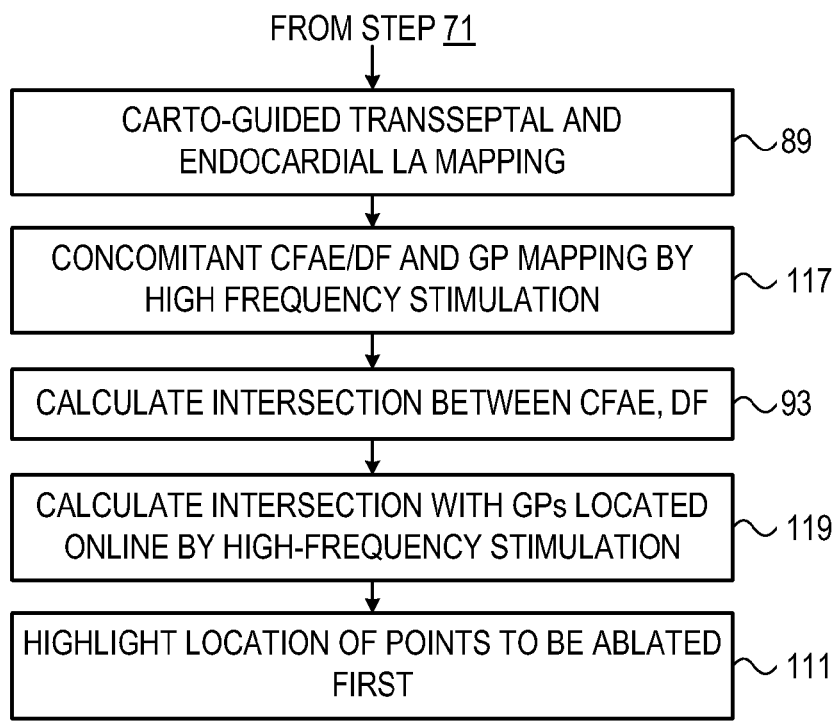
FIG. 6 is a portion of the flow chart shown in FIG. 3, which has been modified in accordance with another alternate embodiment of the invention.

Reference is now made to FIG. 6, which is a portion of the flow chart shown in FIG. 3, and which has been modified in accordance with an alternate embodiment of the invention. In this embodiment, detection of ganglionated plexi is enhanced during the mapping of CFAE and dominant frequency sites as performed in step 93 (FIG. 3) by high frequency stimulation at step 117. Stimulation at 20 Hz, 12 Volts, with a pulse width of 10 ms is suitable. Typically, the use of high frequency stimulation is focused on areas in which ganglionated plexi are anticipated, based on registration of images acquired by the above-describe imaging techniques.

Step 117 defines first regions containing ganglionated plexi by the use of high frequency stimulation, second regions containing CFAE and dominant frequency sites as described above with reference to step 93 (FIG. 3).

Step 93 is performed to define first intersections of second regions (CFAE) with third regions (DF) as described above with respect to FIG. 3. Step 119 is performed to define second intersections of the first intersections and the first regions containing ganglionated plexi as determined by high frequency stimulation. The procedure then continues with final step 111 as described with respect to FIG. 3.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of ablation, comprising the steps of:
    defining first regions containing first locations comprising ganglionated plexi in a heart of a living subject;
    inserting a probe into the heart, the probe having electrodes on a distal portion thereof;
    detecting electrical activity in the heart via the electrodes;
    defining second regions having second locations wherein the electrical activity exhibits a dominant frequency that is higher than a predefined threshold;
    defining third regions having third locations wherein the electrical activity exhibits complex fractionated atrial electrograms;
    constructing an electroanatomical map of the heart that defines intersections of the first regions and at least one of the second regions and the third regions;
    selecting ablation sites within the intersections; and
    ablating cardiac tissue at the ablation sites.

2. The method according to claim 1, further comprising the step of defining fourth regions wherein a contact pressure between the probe and a wall of the heart exceeds a predefined pressure threshold, and wherein the intersections defined in the electroanatomical map comprise intersections of the first regions, the second regions, the third regions and the fourth regions.

3. The method according to claim 1, wherein defining first regions comprises electrically stimulating the heart at a stimulation frequency that exceeds a stimulation threshold.

4. The method according to claim 1, wherein defining first regions is performed by evaluating epicardial fat pads of the heart.

5. The method according to claim 1, wherein defining first regions is performed by at least one of sympathetic cardiac imaging, magnetic resonance imaging, computed tomographic imaging and multi-detector computed tomography.

6. The method according to claim 1, wherein the first regions, the second regions and the third regions are 3-dimensional, and wherein constructing an electroanatomical map comprises displaying the electroanatomical map as at least one 2-dimensional projection.

7. The method according to claim 1, wherein constructing an electroanatomical map comprises defining intersections of the first regions, the second regions and the third regions.

8. The method according to claim 1, further comprising the step of defining segments of the heart, wherein the steps of defining first regions, defining second regions, defining third regions, and selecting ablation sites are performed separately for each of the segments.

9. The method according to claim 1, wherein selecting ablation sites is performed by random selection within the intersections.

10. The method according to claim 1, wherein selecting ablation sites is performed by choosing ones of the second locations and the third locations within the intersections.

11. An ablation apparatus, comprising:
    a flexible probe adapted for insertion into a heart of a living subject and having a distally disposed electrode to be brought into contact with a target tissue in the heart;
    an ablator, which applies a dosage of energy to the target tissue so as to ablate the target tissue at ablation sites therein;
    circuitry for detecting electrical activity in the heart via the electrode;
    a display; and
    a processor linked to the display and the circuitry, the processor operative for:
    defining first regions containing first locations comprising ganglionated plexi in the heart;
    defining second regions having second locations wherein the electrical activity exhibits a dominant frequency that is higher than a predefined threshold;
    defining third regions having third locations wherein the electrical activity exhibits complex fractionated atrial electrograms;
    constructing an electroanatomical map of the heart that defines intersections of the first regions and at least one of the second regions and the third regions; and
    identifying the ablation sites within the intersections on the display.

12. The apparatus according to claim 11, wherein the processor is programmed with image processing software and the step of defining first regions is performed by processing images of the subject using the image processing software.

13. The apparatus according to claim 12, wherein defining first regions is performed by images of epicardial fat pads of the heart.

14. The apparatus according to claim 12, wherein the images of the subject are created by at least one of sympathetic cardiac imaging, magnetic resonance imaging, computed tomographic imaging and multi-detector computed tomography.

15. The apparatus according to claim 11, wherein the processor is operative for defining fourth regions wherein a contact pressure between the probe and a wall of the heart exceeds a predefined pressure threshold, and wherein the intersections defined in the electroanatomical map comprise intersections of the first regions, the second regions, the third regions and the fourth regions.

16. The apparatus according to claim 11, further comprising electrical stimulation circuitry, wherein defining first regions comprises actuating the electrical stimulation circuitry to electrically stimulate the heart at a stimulation frequency that exceeds a stimulation threshold.

17. The apparatus according to claim 11, wherein the first regions, the second regions and the third regions are 3-dimensional, and wherein constructing an electroanatomical map comprises displaying the electroanatomical map as at least one 2-dimensional projection.

18. The apparatus according to claim 11, wherein constructing an electroanatomical map comprises defining intersections of the first regions, the second regions and the third regions.

19. The apparatus according to claim 11, further comprising the step of defining segments of the heart, wherein the steps of defining first regions, defining second regions, defining third regions, and identifying the ablation sites are performed separately for each of the segments.

* * * * *